US00PP26975P2

(12) United States Plant Patent
Warren

(10) Patent No.: US PP26,975 P2
(45) Date of Patent: Jul. 26, 2016

(54) TUPELO TREE NAMED 'JFS-RED'

(50) Latin Name: *Nyssa sylvatica*
Varietal Denomination: JFS-red

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 24 days.

(21) Appl. No.: 14/544,687

(22) Filed: Feb. 4, 2015

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A variety of tupelo tree which combines a unique combination of characteristics in that it combines a narrow growth habit, upright branch angles, elongated oval leaves, and bright, early fall color.

10 Drawing Sheets

Latin name of the genus and species of the plant claimed: *Nyssa sylvatica.*

Variety denomination: 'JFS-red'.

BACKGROUND OF THE INVENTION

In 1999, I decided to initiate a selection program in the species *Nyssa sylvatica* with the intention of improving horticultural characteristics of nursery produced trees. In the summer and fall of each year from 1999 through 2009, I walked numerous rows in a Boring, Oreg. nursery. Each row consisted of hundreds of trees and I examined each tree for desirable horticultural traits. I marked and numbered the very best trees. In the summer of 2005, I discovered a particularly upright three year old tree growing in one of the nursery rows with unusually dark green and attractive foliage. This became my 16$^{th}$ *Nyssa sylvatica* selection discovered as part of this selection program, and I subsequently named it 'JFS-red'. In my evaluation of 'JFS-red' in the autumn of 2005, I noted that it also had unusually bright red fall color.

In March of 2006, I directed the digging and transplanting of 'JFS-red' into a long term experimental evaluation block for further observation in the same Boring, Oreg. nursery. I continued to observe, compare, and evaluate this tree in this location until November 2011, at which time I directed that it be transplanted into an open location in the Boring, Oreg. nursery where it would have more space to grow. I continued my evaluations of this selection at this new location.

Also in March of 2006, I began asexual test propagation of 'JFS-red' by directing the grafting of 20 plants, using common *Nyssa sylvatica* seedlings as rootstock. Of these 20 grafting attempts, 17 were successful and resulted in viable plants of 'JFS-red'. In May, 2007, I transplanted the strongest eight of these plants into a nursery row, and in June of 2008, I transplanted an additional five plants into a different nursery row location, both being in the same Boring, Oreg. nursery. I then destroyed the remaining four grafted plants. For the purpose of additional test propagation, I chip budded four *Nyssa sylvatica* 'JFS-red' seedlings in another nursery row in the Boring, Oreg. nursery in August of 2008. Three of the chip budded trees grew successfully from this trial, and the failed tree was destroyed. In each of the three instances of test growing of 'JFS-red', I observed and evaluated the trees for the following three years. Of these test propagated trees, seven were retained and transplanted into a stock block location in anticipation of future propagation. The remaining test propagated trees were destroyed.

All of this asexual propagation of my new variety in Boring, Oreg. by grafting and budding on *Nyssa sylvatica* rootstock has shown that the characteristics of my new tree are firmly fixed in successive generations. Testing, evaluation, and comparison of 'JFS-red' with seedlings of the species and existing commercial cultivars of *Nyssa sylvatica* has convinced me that my new tree has superior form and appearance for landscape use.

SUMMARY OF THE INVENTION

This new cultivar possesses a unique combination of characteristics in that it combines a narrow growth habit, upright branch angles, elongated oval leaves, and bright, early fall color.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
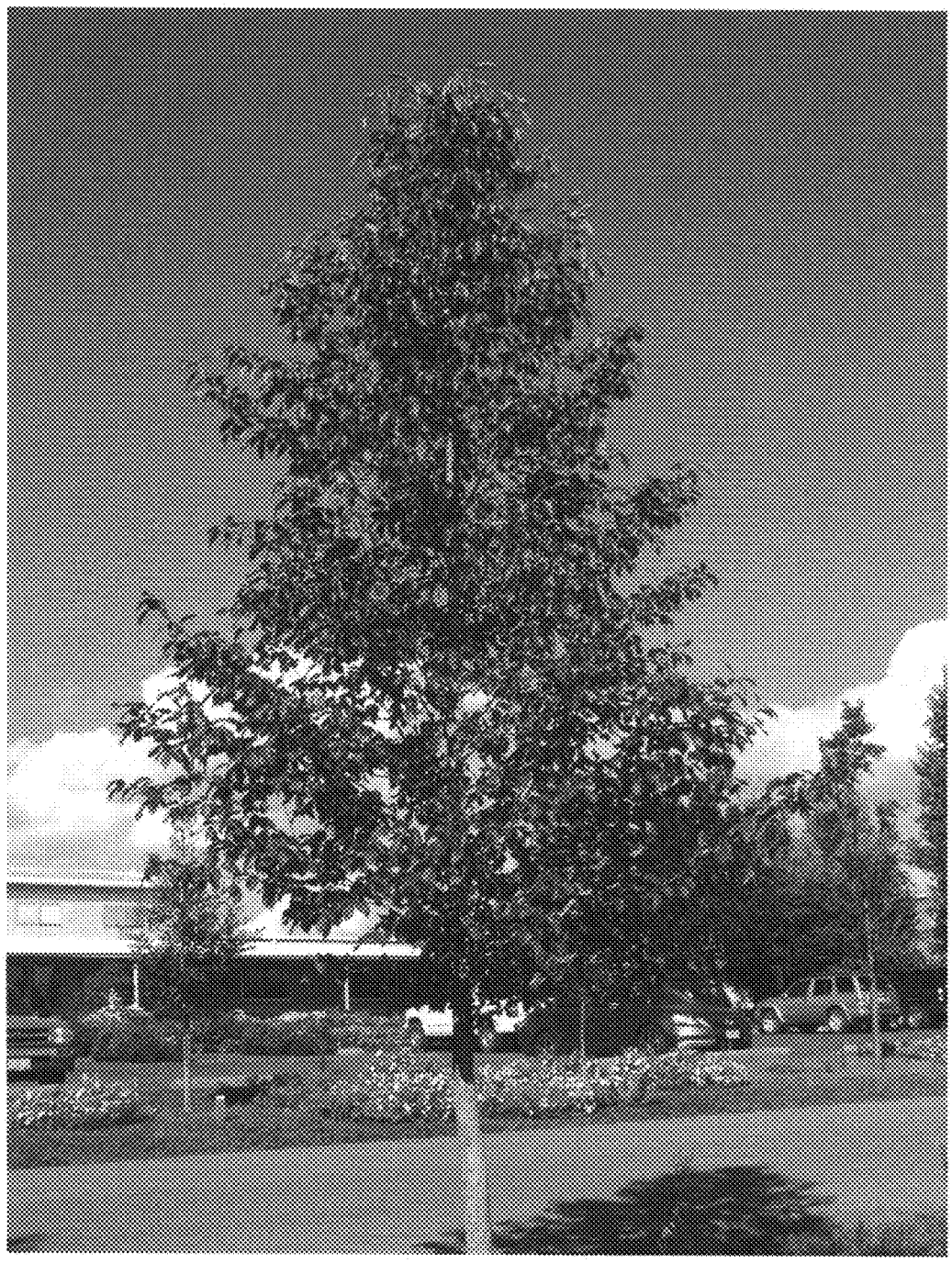
FIG. 1: Illustrates the original tree at 12 years of age in summer foliage, showing its narrowly pyramidal shape and upright growth habit.
Figure 2:
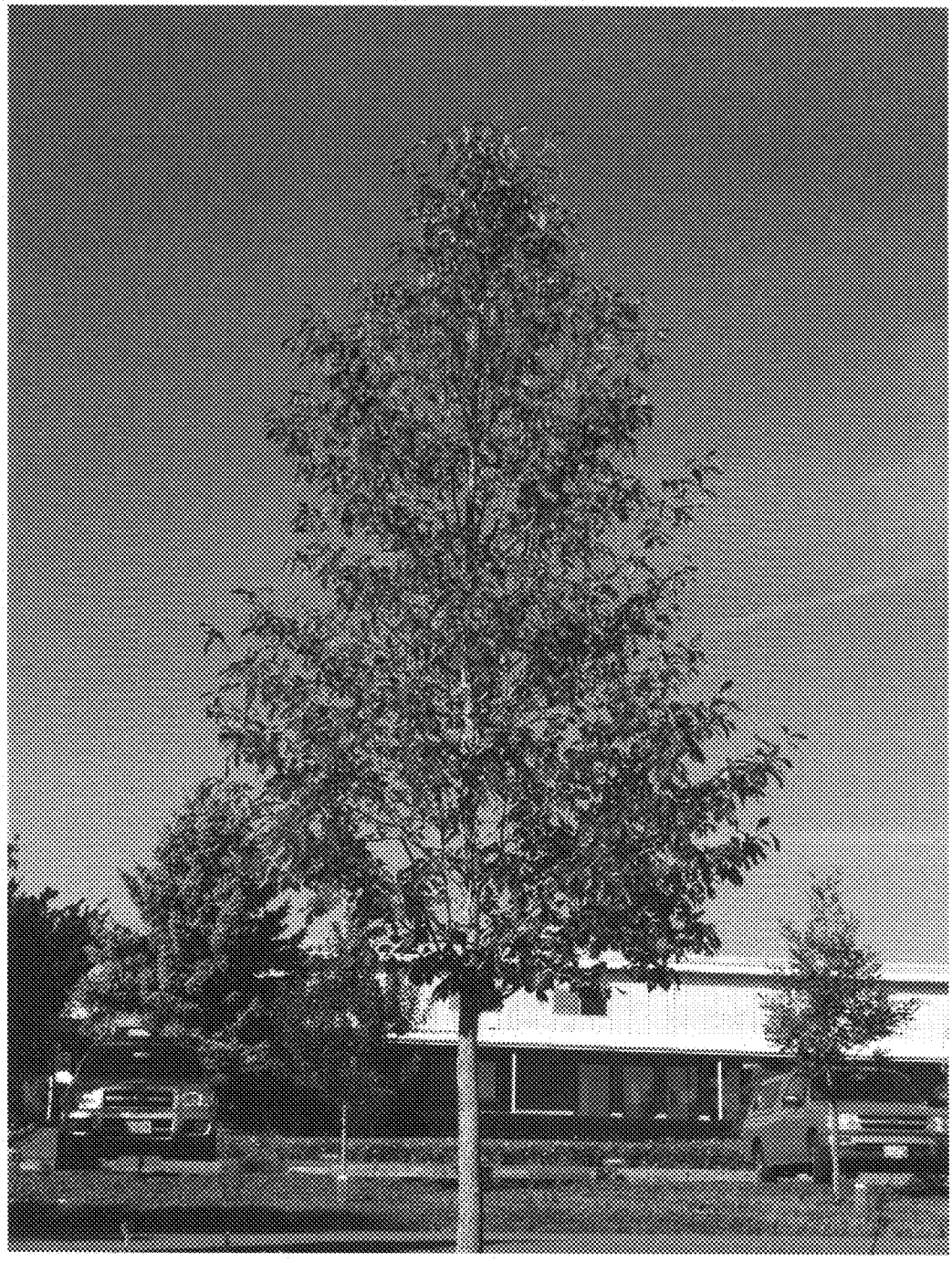
FIG. 2: Illustrates the original tree at 12 years of age in fall color, showing its early peak fall color on Oct. 16, 2014.
Figure 3:
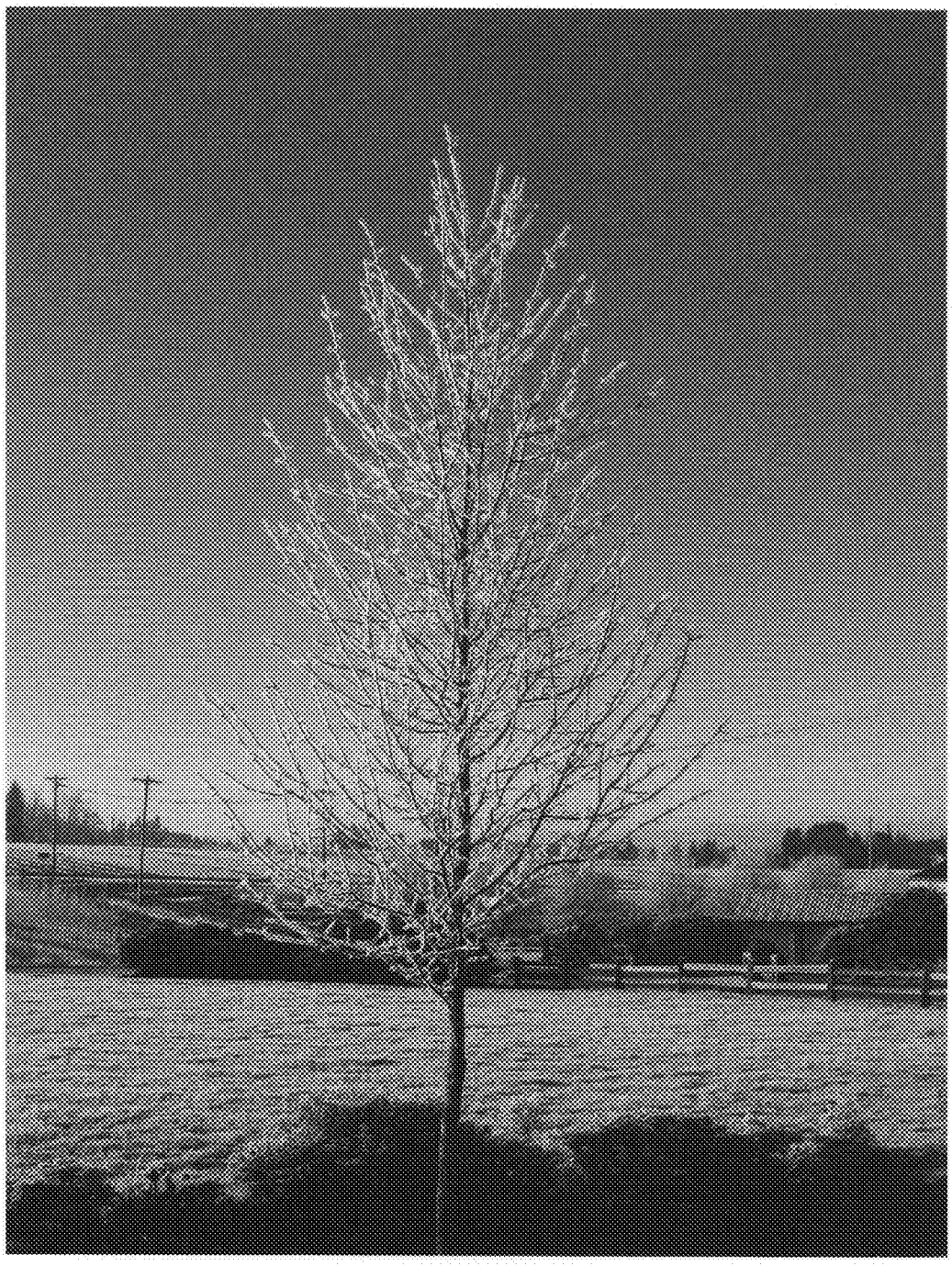
FIG. 3: Illustrates the original tree in winter dormancy at 11 years of age, showing its uniform branch angle of 40° to 60°. Frost accents the branches in this photo.
Figure 4:
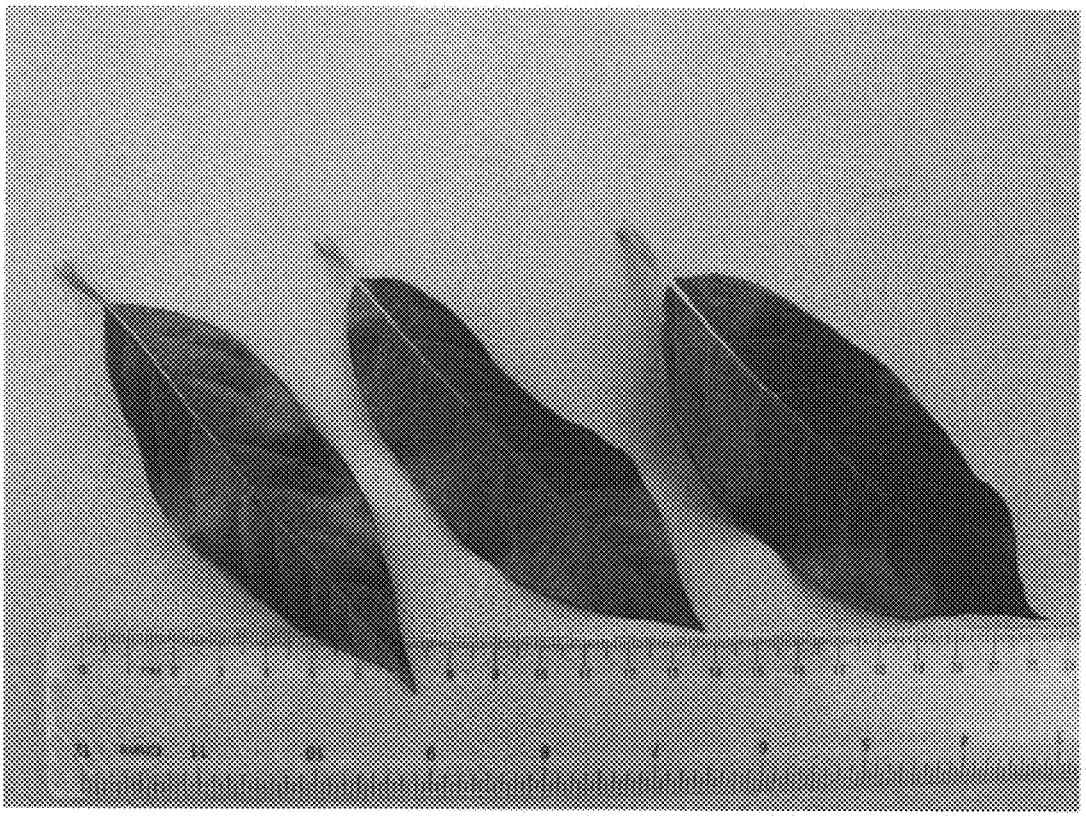
FIG. 4: is a close up of the top surface of summer foliage, showing the typical elongated oval shape of the leaves and the acuminate tip.
Figure 5:
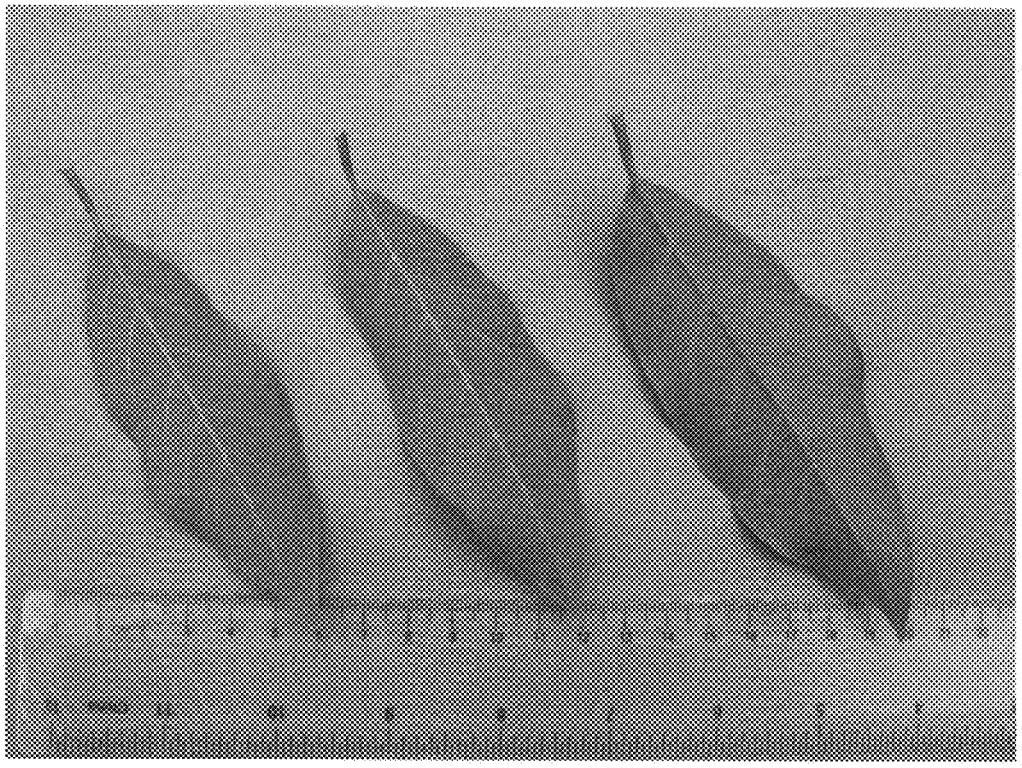
FIG. 5: is a close up of the lower surface of the late summer foliage, showing typical leaf shape and color, with the mid vein showing the initial progression toward fall color.
Figure 6:
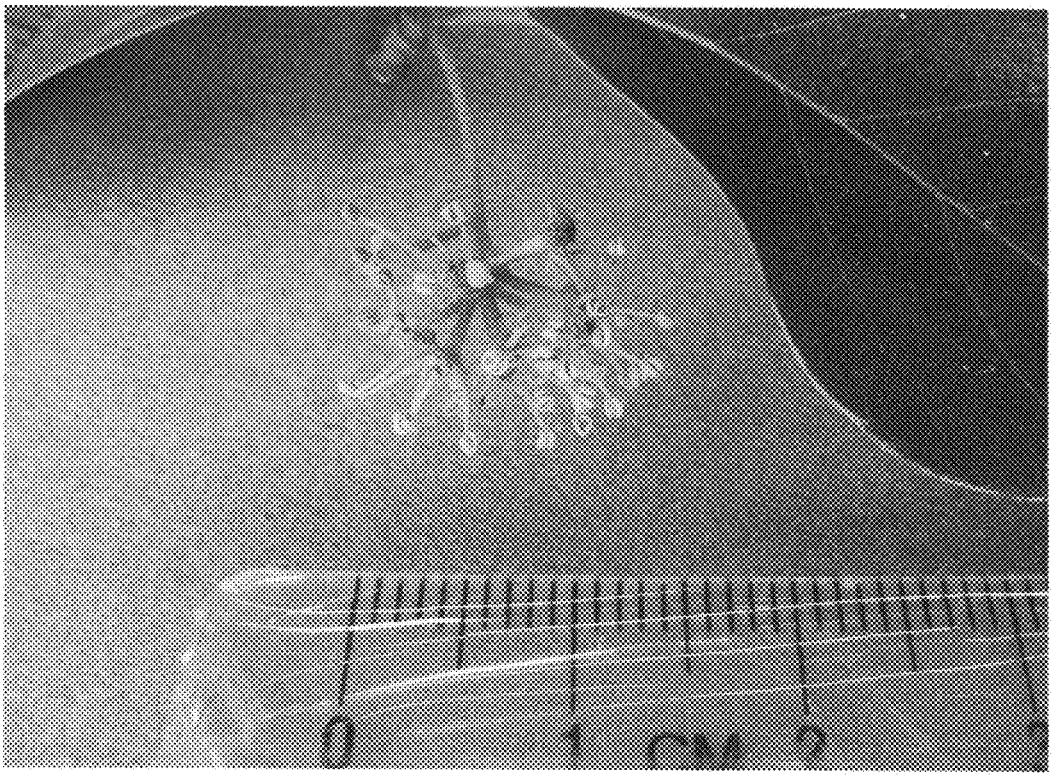
FIG. 6: is a close up of the flowers showing the globose raceme.
Figure 7:
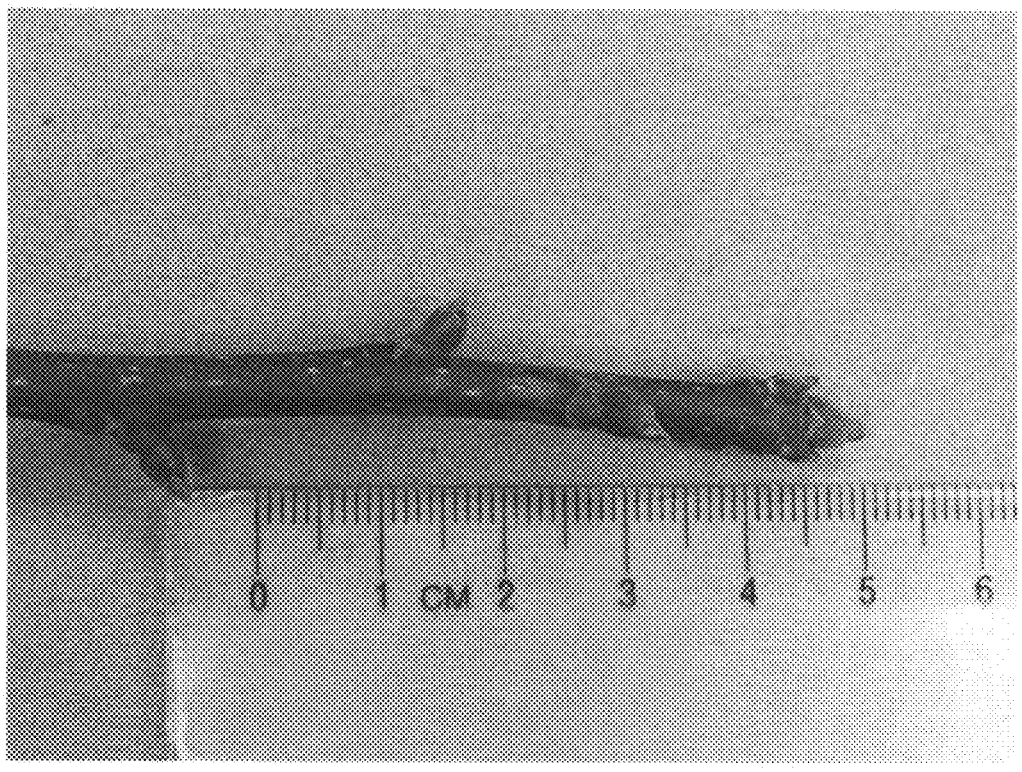
FIG. 7: is a close up of a terminal twig showing the shape of terminal and lateral buds.
Figure 8:
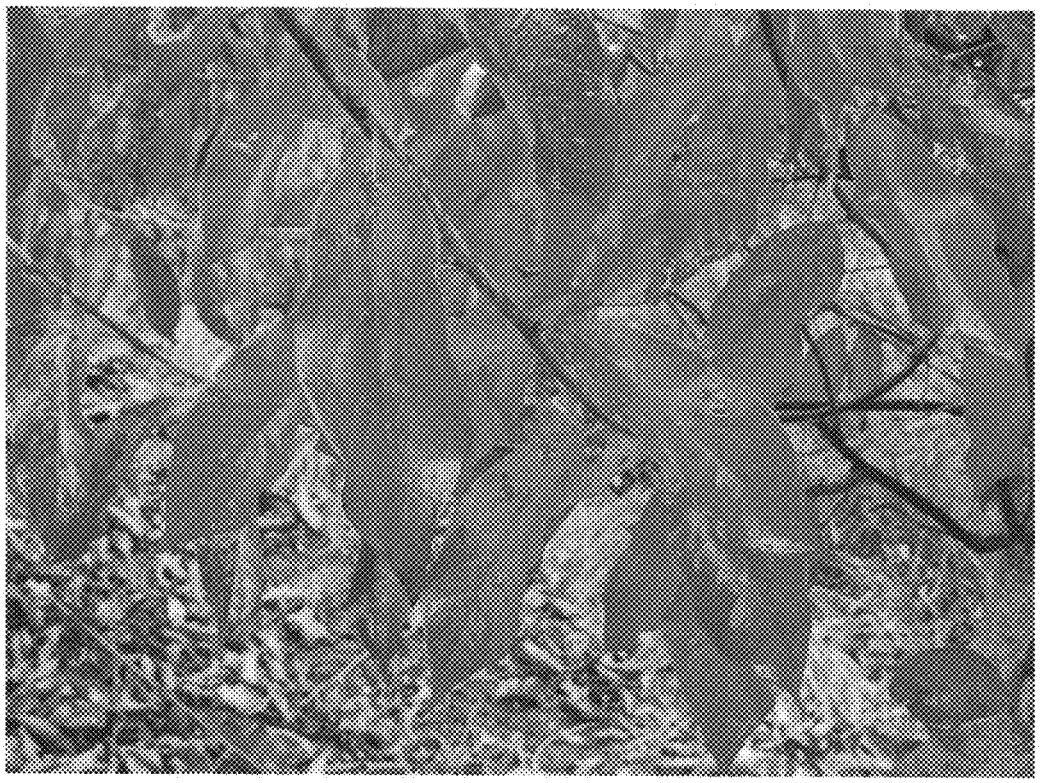
FIG. 8: is a close up of the foliage showing typical fall color.
Figure 9:
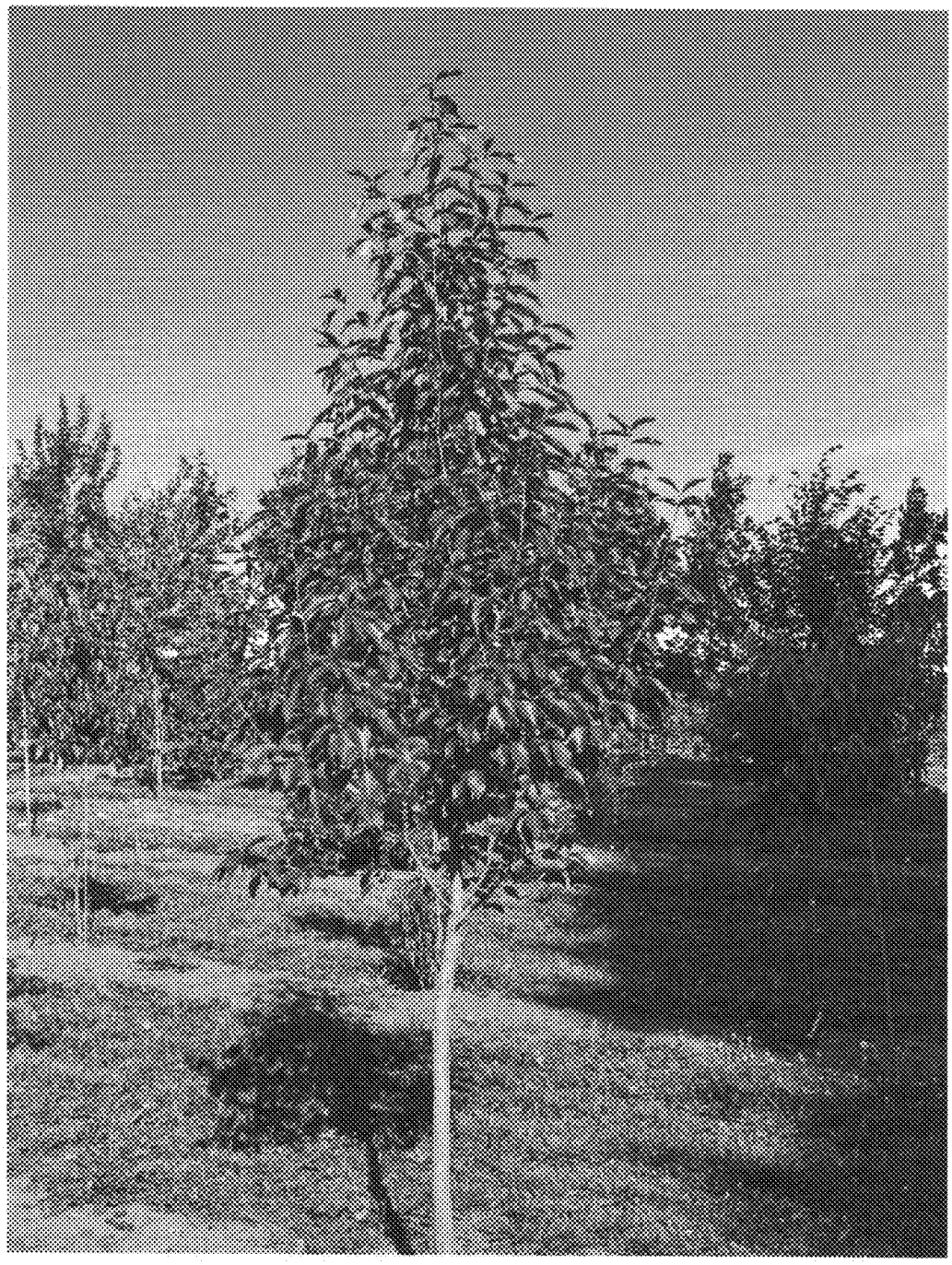
FIG. 9: is a photo showing the early initiation of fall color in late September showing that the inner leaves of the tree color brightly before the outer leaves.
Figure 10:
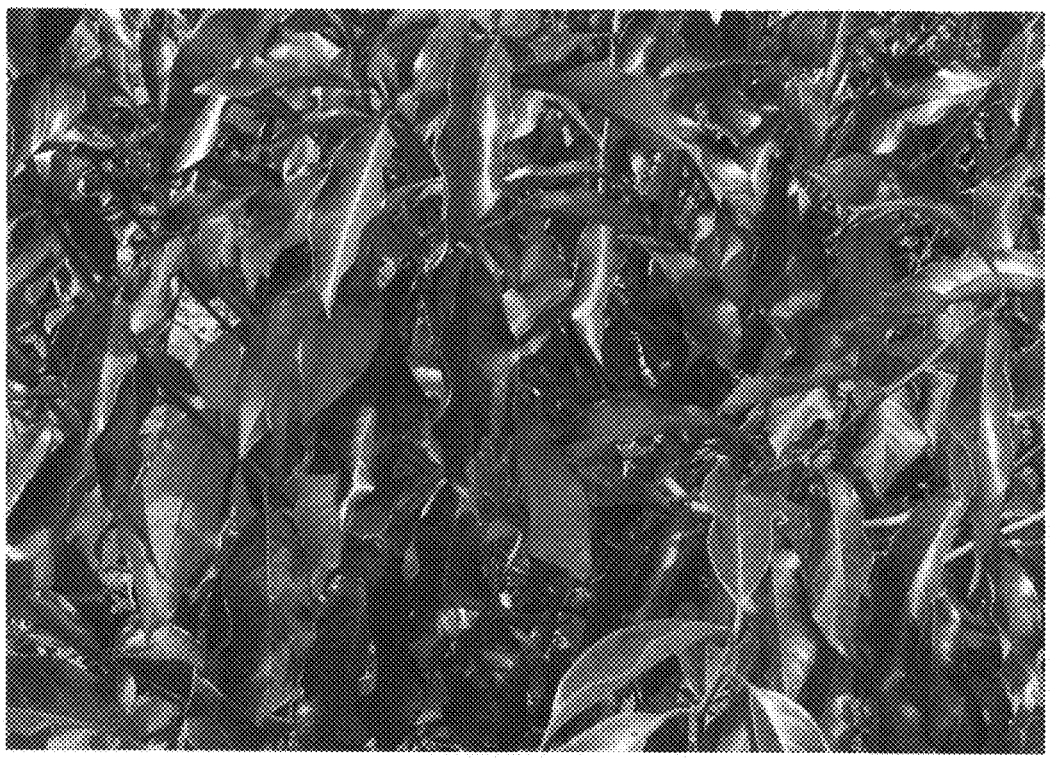
FIG. 10: is a close up of the initiation of fall color in late September showing the brightly colored fall color of the inner leaves being displayed while the outer leaves are still in summer color.

The following detailed description of the 'JFS-red' variety is based on observations of the original tree and one, two, and three year old progeny asexually propagated by grafting and chip budding. The observed progeny were trees which were growing in Boring, Oreg. The following is a detailed description of my new tupelo tree with color descriptions using terminology in accordance with The Royal Horticultural Society (London) Colour Chart© 1986, except where ordinary dictionary significance of color is indicated. 'JFS-red' has not been tested under all possible conditions hence, phenotypic differences may be observed with variations in environmental conditions without any variance in genotype.

Scientific name: *Nyssa sylvatica* 'JFS-red'.

Parentage:

*Seed parent*.—Unknown tree of the species *Nyssa sylvatica*, not patented.

*Pollen parent*.—Unknown tree of the species *Nyssa sylvatica*, not patented.

Tree:

*Overall shape*.—Narrowly pyramidal, symmetrically branched, and strongly upright.

*Height*.—4.9 meters at 12 years of age.

*Width*.—2.0 meters at 12 years of age.

*Trunk diameter*.—9.9 cm at 10 cm height above ground and 7.0 cm at 1 meter above ground, both at 12 years of age.

*Trunk*.—Trunk bark texture: Smooth when young, generally for about the first eight years of life, gradually becoming rough and vertically fissured by the 12$^{th}$ year under conditions in Boring, Oreg. Trunk bark color: Immature bark color: Brown 200C to Brown 200D. Mature bark color: Greyed-green 197B to Grey-brown 199C. Lenticels: Small, inconspicuous, rounded, 0.5 to 1.0 mm in diameter, Greyed-green 198D. Lenticels disappear in the bark by age eight.

*Primary branches*.—Upward angled at 40° to 60° from the trunk when measured 30 cm along the branch from the trunk.

*Branch color*.—Brown 200C at branch tips to Greyed-green 197B at the branch base.

*Branch lenticels*.—Rounded, 0.5 to 1.0 mm in diameter, Greyed-green 198D.

*Dormant buds*.—Imbricate, ovoid with an acute tip. Bud scales are slightly pubescent on the margins and more pubescent at the tips. Terminal buds are 5 mm to 7 mm long by 3 mm to 5 mm in width on branches of 4 year old trees. Lateral buds are slightly smaller, generally 3 to 5 mm long by 2 mm to 3 mm in width.

*Bud break*.—Bud break averages April 10$^{th}$ in Boring, Oreg.

*Internodes*.—Typically 3 cm to 5 cm long when measured at the midpoint of a branch on a 4 year old tree. Internodes are slightly shorter on older trees and are reduced to approximately 1 cm at branch tips.

*Hardiness*.—Has tolerated field temperatures to 10 degrees F. without damage in Boring, Oreg. This is the minimum temperature this location experienced during the life of the trees of my new variety. It is believed to have Zone 5 cold hardiness similar to other plants of this species.

*Disease resistance*.—Appears similar to the species with no differences noted.

Leaves: Except as otherwise noted, observations are from twenty vigorous growth leaves taken from the middle of branches of 4 year old trees in Boring, Oreg.

*Arrangement*.—Alternate.

*Type*.—Simple.

*Texture*.—Smooth.

*Sheen*.—Satiny to slightly glossy.

*Length*.—10 cm to 14 cm.

*Width*.—4 cm to 6 cm.

*Petioles*.—13 mm to 18 mm long by 2 mm in diameter.

*Overall shape*.—Elongated oval.

*Margin*.—Smooth.

*Tip*.—Acuminate.

*Base*.—Broadly acute.

*Stipules*.—None.

*Spring leaf color*.—First emerging leaves are Yellow-Green 146C with a tint of Greyed-Red 181A along the leaf margins. Summer Leaf Color: Upper leaf surface: Green 139A to Yellow-green 147A. Lower leaf surface: Yellow-Green 147B. Vein: Yellow-Green 145B to 145C. The center vein begins to display a tint of Red 43D to Red 43C in late summer.

*Fall leaf color*.—Upper leaf surface: Varies in a range from Red 42B to Red 46A with Red 45A being the dominant color. Lower leaf surface: Red 42B to Red 45A.

*Timing of fall leaf color*.—Average dates for original tree in Boring, Oreg.: Onset: September 30. Peak: October 16. Latest extent of red fall color: October 28. Fall color begins and peaks about seven days earlier than is typical of seedling trees of the species *Nyssa sylvatica*. Fall color typically begins on inner leaves and progresses to the outer leaves.

*Defoliation*.—Average date for complete defoliation of the original tree in Boring, Oreg.: October 29.

*Pubescence*.—None.

*Persistence*.—The tree is deciduous.

Flowers:

*Overall*.—The tree is dioecious and has only male flowers. Seven to ten small flowers are borne in head-like, globose racemes. These globose racemes average 16 mm in diameter.

*Shape*.—Individually, each flower is a very small whorl of stamens.

*Size*.—Individual flowers have an average diameter of 8 mm.

*Color*.—Yellow-Green 146C to 137C.

*Petals*.—Insignificant; appear as tiny bracts, 1.0 to 2.0 mm long by 0.5 mm wide, generally five per flower. Yellow-Green 146C.

*Sepals*.—None.

*Stamen*.—2 mm to 3 mm lone by 0.5 mm in diameter. Yellow-Green 146C.

*Anthers*.—Broadly oval but slightly irregular in shape, 1.0 mm long by 0.7 mm to 0.9 mm in diameter, with two distinct lobes. Yellow-Green 154A.

*Pollen*.—Yellow 10B.

*Pedicel*.—Length 2 mm to 4 mm; diameter 0.5 mm; color Yellow-Green 146C.

*Peduncle*.—1 cm to 2 cm long by 0.5 mm to 0.8 mm diameter.

*Pubescence*.—None.

*Fragrance*.—None.

*Flowering date*.—All based on Boring, Oreg. average dates.

*First bloom*.—May 25.

*Peak bloom*.—June 2.

*End of bloom*.—June 6.

Fruit: None.

Comparison to other varieties: The following comparisons and measurements relative to the unpatented species are based on four year old trees growing adjacent to each other in a Boring, Oreg. nursery field. The shape of trees of my new variety is narrowly oval to narrowly pyramidal while typical seedling trees of the same age are broadly pyramidal. The branches of my new tree are upright and grow at typical angles of 40 to 60 degrees when measured 30 cm from the trunk, while seedling trees of the species have typical branch angles of 90 to 130 when measured in the same way. Additionally, my new tree produces trees that are elongated oval in shape while typical seedling trees of the species have leaves that are more broadly oval; when measured, the leaves of my tree had a typical length to width ratio of 2.49 to 1, while seedling leaves of the species had a length to width ratio of 2.00 to 1. My new variety 'JFS-red' can be distinguished from other patented cultivars of *Nyssa sylvatica* in the following ways. 'WFH1' (U.S. Plant Pat. No. 22,976) is a female clone, produces pistillate flowers, and produces fruit, while my new variety is male, produces no pistillate flowers, and no fruit. 'Nsuhh' (U.S. Plant Pat. No. 22,951) has very glossy leaves while the leaves of my new tree are satiny to slightly glossy. In addition, the upper leaf surface of the first emerging leaves of 'Nsuhh' is Yellow-Green 144A while the upper leaf surface of the first emerging leaves of my new tree is Yellow-Green 146C, and the lower surface of young developing leaves of 'Nsuhh' is pubescent while leaves of my new tree are glabrous at this stage. 'NXSXF' (U.S. Plant Pat. No. 11,391) is polygamodioecious and produces both male and female flowers, with most flowers being female. In contrast, my new tree is dioecious and produces only male flowers. 'NXSXF' produces fruit while my tree produces none. In addition, 'NXSXF' has a typical branch angle of 60° to 80° at the base and 20° to 30° near the top while my tree has a more uniform typical branch angle of 40° to 60°. When compared to seven named cultivars of *Nyssa sylvatica* in Boring, Oreg., my new tree had the earliest development of peak fall color. My new tree developed peak fall color on average on October 16 in Boring, Oreg., while comparison cultivars developed peak fall color between October 21 and November 5. The comparison cultivars were 'WFH1', 'NSUHH', 'NXSXF', 'JFS-PN Legacy1' (not patented), 'David Odom' (not patented), 'Wildfire' (not patented), and 'Haymanred' (not patented). This demonstrates that my new tree develops unusually early fall color.

I claim:

1. A new and distinct variety of tupelo tree, substantially as herein shown and described.

* * * * *